United States Patent
Solberg

(10) Patent No.: US 8,480,451 B2
(45) Date of Patent: Jul. 9, 2013

(54) ADHESIVELY SUPPORTING A BREASTSHIELD

(75) Inventor: Jill M. Solberg, Woodstock, IL (US)

(73) Assignee: Medela Holding AG (CH)

( * ) Notice: Subject to any disclaimer, the term of this patent is extended or adjusted under 35 U.S.C. 154(b) by 598 days.

(21) Appl. No.: 12/116,732

(22) Filed: May 7, 2008

(65) Prior Publication Data

US 2008/0287037 A1    Nov. 20, 2008

Related U.S. Application Data

(60) Provisional application No. 60/938,344, filed on May 16, 2007.

(51) Int. Cl.
*A41C 3/00* (2006.01)
*A61M 1/06* (2006.01)

(52) U.S. Cl.
USPC ............... 450/37; 604/346; 604/74; 604/317

(58) Field of Classification Search
USPC .............. 450/36–38, 54–57; 604/343–346, 604/317, 74–76; 119/14.12
See application file for complete search history.

(56) References Cited

U.S. PATENT DOCUMENTS

| | | | | |
|---|---|---|---|---|
| 4,870,977 A | * | 10/1989 | Imonti | 128/890 |
| 5,423,783 A | * | 6/1995 | Battles et al. | 604/344 |
| 5,514,166 A | * | 5/1996 | Silver et al. | 604/74 |
| 6,821,185 B1 | * | 11/2004 | Francis | 450/36 |
| 6,962,519 B1 | * | 11/2005 | Clark | 450/37 |
| 6,974,361 B2 | * | 12/2005 | Cravaack et al. | 450/36 |
| 7,175,502 B2 | * | 2/2007 | Clark | 450/37 |
| 7,607,965 B1 | * | 10/2009 | Frazier | 450/36 |
| 7,785,305 B2 | * | 8/2010 | Myers et al. | 604/327 |
| 7,789,865 B2 | * | 9/2010 | Myers et al. | 604/327 |
| 2001/0031911 A1 | | 10/2001 | Khouri | |
| 2003/0004459 A1 | | 1/2003 | McKendry et al. | |
| 2006/0074379 A1 | | 4/2006 | Hunt | |

OTHER PUBLICATIONS

International Search Report for PCT/US2008/062913 mailed Sep. 24, 2008.
"Medical Market Solutions for Converters," 2006, 3M Industrial Business Markets.
"Your guide to ostomy adhesives," 2007, Coloplast A/S, Denmark.

* cited by examiner

*Primary Examiner* — Gloria Hale
(74) *Attorney, Agent, or Firm* — McDonnell Boehnen Hulbert & Berghoff LLP

(57) ABSTRACT

A breastshield is provided that may be adhesively secured to a mother's breast for use in a breastpumping system. The adhesive is sufficiently strong so as to independently support the breastshield in position throughout a breast pumping session, including supporting the milk container, thereby enabling the mother to participate in other activities during the pumping session. The adhesive is advantageously of a type that is readily removed from the breast with the breastshield, and most preferably without leaving any significant residue.

20 Claims, 11 Drawing Sheets

ADHESIVELY SUPPORTING A BREASTSHIELD

REFERENCE TO RELATED APPLICATIONS

This application is a non-provisional application claiming priority under 35 U.S.C. section 119(e) to provisional application No. 60/938,344 filed May 16, 2007, the contents of which are incorporated herein by reference.

BACKGROUND

1. Field of the Application

The invention relates generally to breastpumps. More particularly, the present invention relates a system for adhesively supporting a breast shield, as well as related breast pump equipment, on a woman's breast, and a method of using the same.

2. Description of the Related Art

Breastpumps for the purpose of extracting breastmilk from a nursing mother are well-known and generally comprise: a breastshield (also known as a hood) that is typically funnel-shaped and fits over the breast; a pressure source, typically vacuum, connected to the breastshield for generating an intermittent vacuum within the breastshield such that milk is expressed from the breast; and a conduit structure for communicating milk from the breastshield to a receptacle for the expressed milk, as well as for communicating pressure variations (such as the foregoing vacuum) to the breastshield. There are occasions when mothers cannot conveniently plug a breastpump into an external vacuum source or an electrical outlet is not available. In those instances, battery-powered or manual breastpumps may be used to express milk.

Manually-operated breastpumps typically must be operated by two hands: one to hold the breastshield in place and the other to drive the pump (e.g., a piston cylinder). A number of the pumps do provide for one-handed use, but still plainly require the use of a mother's hand(s) to operate or support the pump—such as when double-pumping using a motor-driven pressure source—thus limiting the mother's activities, and in some instances preventing the mother from accomplishing any other task while she is expressing milk.

U.S. Pat. No. 5,514,166 to Silver et al. describes one attempt at breast shield support, such as a garment, for supporting a breastshield of a breast pump upon a woman's breast in a "hands-free" manner. While useful in freeing up the mother's hands for other activity, these and similar "hands-free" arrangements generally require a separate garment, special bra, or other accessories and accoutrements to keep the breastpump assembly in place, especially if also supporting the milk container.

Thus, it would be advantageous to provide a mother with something that could be simply and readily used to permit her to use a breastpump, while also allowing her the free use of her hands to perform other tasks, yet does not require any extra or special garment. It would likewise be useful to provide such a solution that is reusable, or alternatively inexpensive enough to be disposable.

SUMMARY OF THE INVENTION

The present invention variously meets these foregoing objectives, and more, by providing a breastshield that may be adhesively secured to a mother's breast for use in a breast-pumping system. The adhesive is sufficiently strong so as to independently support the breastshield in position throughout a breastpumping session, including supporting the milk container, thereby enabling the mother to participate in other activities during the pumping session. The adhesive is advantageously of a type that is readily removed from the breast with the breastshield, and most preferably without leaving any significant residue.

In one embodiment, the breastshield is provided with a separate adhesive pad that has a layer of adhesive on one side covered by release paper. The pad is placed on the breastshield, as on the back (outward facing) side. A portion of the pad extends beyond the breastshield, and attaches to the breast, thereby adhering the breastshield in place. Alternatively, a double-sticky pad can be provided, which would have one side adhered to the front (inboard) side of the breastshield, and the other side adhered to the breast.

In another embodiment, a yoke-like device is provided with a center ring from which extend arms ending in adhesive tabs. The center ring releasably fits about the nipple tunnel of the breastshield, with the arms extending outwardly therefrom. The tabs are used to secure the breastshield to the breast (or chest).

In yet another embodiment, a sling-like support strap is provided with adhesive pads at each end. Once the breastshield is placed on the breast, one of the pads is affixed to the breast or chest. The support strap then is directed in a downwardly direction, passed under the nipple tunnel of the breastshield, and then directed in an upwardly direction. The remaining pad is then affixed to the breast or chest, thereby supporting the breastshield assembly and retaining the breastshield in place.

In still another embodiment, a sleeve designed to conform to the outside of the breastshield has a ring of adhesive about its circumference that is to be placed over a breastshield. The sleeve fits over the breastshield and is pressed against the breast for the adhesive to adhere the assembly to the breast.

In a further embodiment, the breastshield is provided with a separate mounting ring having a flange preferably constructed of a soft pliable material positioned along the ring's inner circumference. Adhesive is provided along one side of the ring. With the ring adhered to the mother's breast/chest, the outer perimeter of the breastshield is then slid (wedged) behind the flange, thus retaining the breastshield in place. Alternatively, an interior annular channel can be provided in the ring, within which the perimeter edge of the breastshield is received to mount the breastpump assembly.

While the invention can be used for a single breastpump assembly, in general, all of these embodiments yield a system providing for hands-free simultaneous expression of milk from both breasts. Two breastpump assemblies are connected via a neck strap that is intended to be worn around a mother's neck. Each breastshield is then further provided with a support strap that performs much like a tether having adhesive pads at each end for positioning the shield on the breast. With the breastshields in place, the neck strap is placed about a mother's neck. The tether straps are positioned over the top of the respective nipple tunnels, with the ends of the straps then secured in place below the height of the breastshield on either side, for a secure positioning of the breastpump assemblies.

These as well as other aspects and advantages of the invention will become further apparent to those of skill in the art by reading the following detailed description, with reference where appropriate to the accompanying drawings. Further, it should be understood that the embodiments described herein are intended to illustrate the invention by way of example only.

BRIEF DESCRIPTION OF THE DRAWINGS

Exemplary embodiments of the invention are described herein with reference to the drawings, in which.

DETAILED DESCRIPTION OF EMBODIMENTS OF THE INVENTION

The present invention is described herein largely with respect to embodiments that use a conventional breastpump assembly. The standard breastpump assembly components are therefore largely unaltered, and need not be adapted to implement this invention. This embraces the utility of the invention, since specialty breastshields or related componentry need not be made or adapted to use the invention. Some embodiments nonetheless are shown with breastshields somewhat adapted for use of the invention, but presenting further useful advantages. Other adaptations can be made with breastshield changes to further enhance the interface and ease of use and reuse, such as in instances discussed herein. For general details, the breastpump assembly comprises: a breastshield that is typically funnel-shaped and fits over the breast; a vacuum source connected to the breastshield for generating an intermittent pressure within the breastshield such that milk is expressed from the breast; and a conduit structure for communicating milk from the breastshield to a receptacle for the expressed milk, as well as for communicating pressure variations (such as a vacuum) to the breastshield.

Reference can be made to U.S. Pat. Nos. 5,776,098 and 6,676,631 for general details of a breastpump assembly and its operation.

Figure 1A:
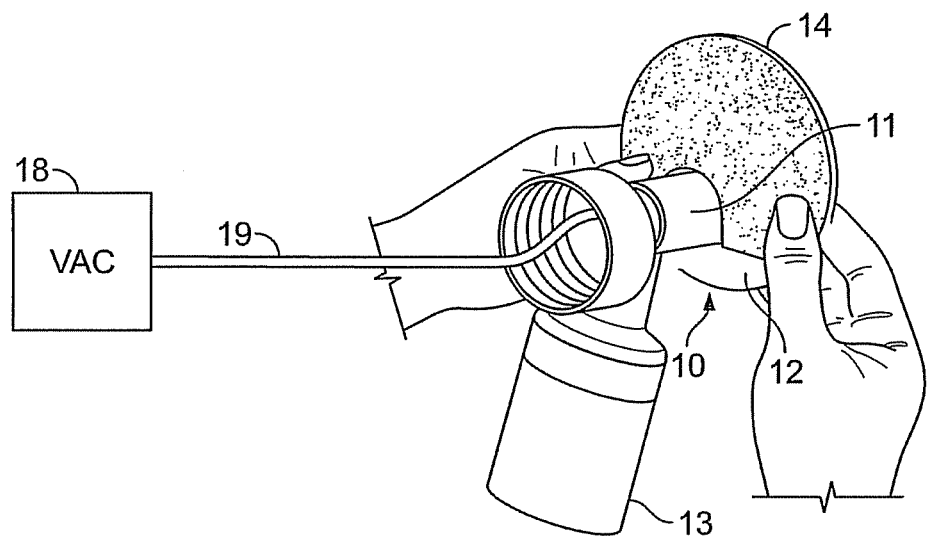
FIG. 1(a) is a perspective view of a first embodiment made in accordance with the present invention.
Figure 1B:
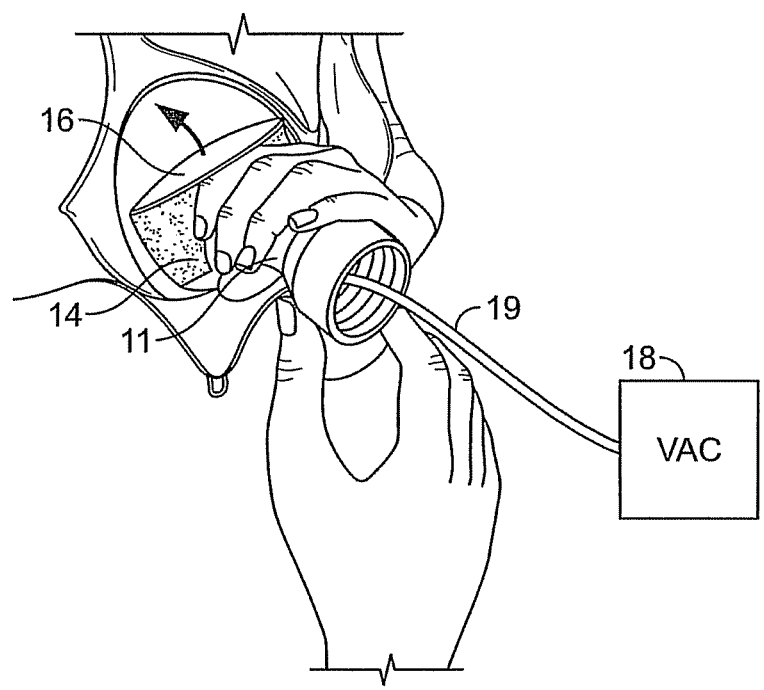
FIG. 1(b) is a perspective view of the first embodiment being adhered to a mother's breast.

Referring to FIGS. 1(a)-(d), one embodiment of the present invention is depicted. A breastshield 10 has a central portion 12 and a nipple tunnel 11 of extending therefrom. Consistent with a conventional breastpump assembly, tubing 19 extends between an internal conduit structure to a vacuum source 18. A milk collection container 13, as depicted in FIG. 1(a) is also connected to the conduit structure. These details of the breastpump assembly are, again, well known in the art.

Figure 1C:
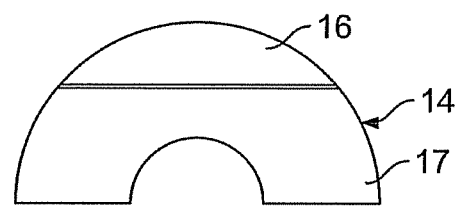
FIG. 1(c) is a rear view of the adhesive pad of the first embodiment of the present invention.

This embodiment further includes a separate adhesive pad 14 in the general shape of an ellipse-like structure. The pad 14 can be made of a non-woven, thin plastic, polyethylene or rubber material, just to name a few possibilities, and has a layer of adhesive 15 on one side, the adhesive being covered by a release paper. The exact nature of the pad 14 is non-limiting, being a stock item in the art. The material is much like the variety that is used with standard adhesive bandages. Referring to FIG. 1(c), a first part of the release paper 16 covers the adhesive on the upper portion of the pad and a second part of the release paper 17 covers the adhesive on the lower portion of the pad. A single (integral) release paper could also be used.

Figure 1D:
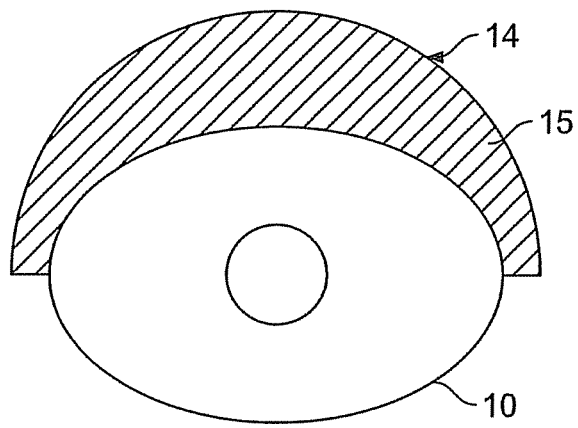
FIG. 1(d) is a front view of the first embodiment of the present invention (as viewed in use)

In use, release paper part 17 is removed and the pad 14 is placed over the top portion of the breastshield 10. The adhesive on the lower portion of the pad adheres the pad 14 to the breastshield 10. The breastshield 10 is then positioned on the breast. If the area of the pad 14 covered by release paper part 17 extends beyond the perimeter of the shield, that portion can be pressed lightly so that the adhesive on the lower portion of the pad holds it in position. Thus, the pad 14 positions a portion of the breastshield between the adhesive pad and the breast. With the breastshield 10 in place, release paper part 16 is removed (FIG. 1(b)) and the upper portion of the adhesive pad 14 is adhered to the skin. FIG. 1(d) depicts the breastshield with both release paper parts removed and adhered to the shield 12. With this embodiment of the present invention, a mother may proceed with expressing milk without having to support the pump with her hand(s) and is free to participate in other activities during the pumping session. It would be expected that a mother would be using two breastpump assemblies attached in this manner at the same time. When desired (such at the end of the pumping session), the adhesive pad 14 is readily removed from the breast with the breastshield 10, and preferably without leaving any significant adhesive residue. This embodiment may be disposable after one use (although as noted below, it could also be made reusable).

Figure 1E:
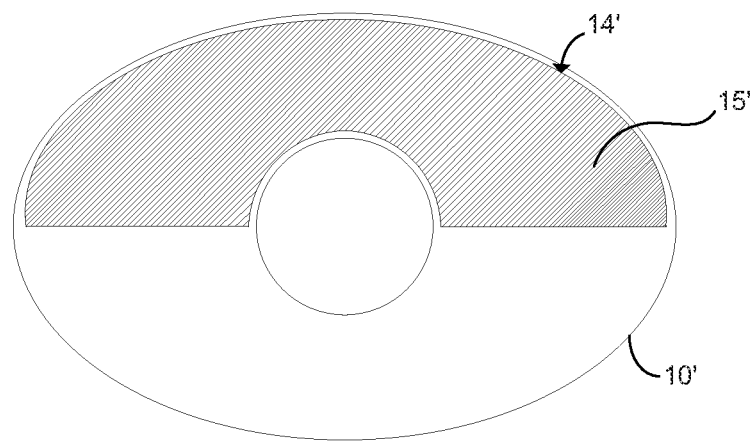
FIG. 1(e) is a front view of another embodiment of the present invention (as viewed in use).

FIG. 1(e) depicts another embodiment of the present invention, wherein a double-sticky pad 14' can be provided with a layer of adhesive 15' on both sides, which would have one side adhered to the front (inboard) side of the breastshield 10', and the other side adhered to the breast.

Figure 2A:
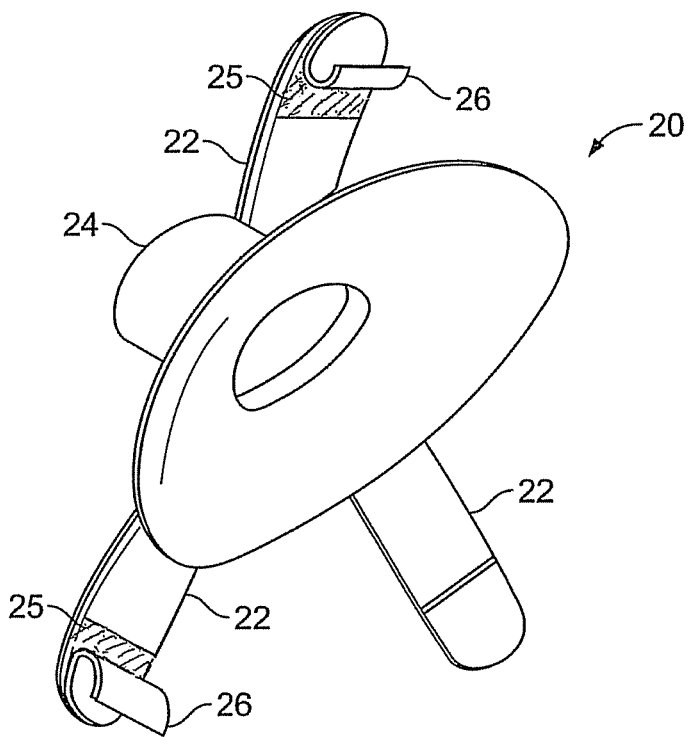
FIG. 2(a) is a perspective view of a second embodiment made in accordance with the present invention.
Figure 2B:
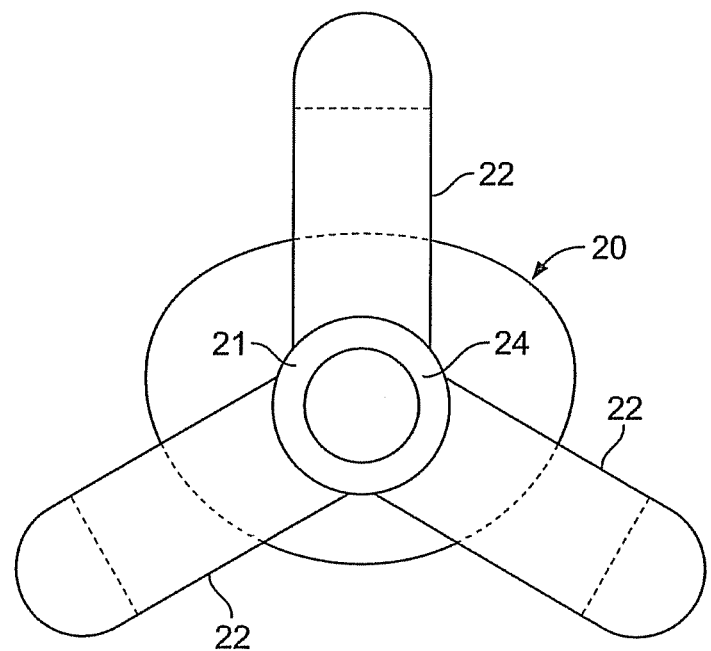
FIG. 2(b) is a rear (back) view of the second embodiment of the present invention (as viewed in use)

FIGS. 2(a) and (b) depict another embodiment of the present invention. A breastshield 20 is shown in conjunction with an attachment device having a center ring 21 with a number of tabs 22. The embodiment is depicted with three tabs; alternately, a different number of tabs may be used to secure the breastshield to the breast without departing from the scope of the invention.

The center ring 21 fits about the nipple tunnel 24 of the breastshield 20 and the tabs 22 extend radially outwardly from the center ring 21. The center ring 21 may be an integral piece that is slid over the nipple tunnel 24, or alternately may be provided with a separation that allows the ring to fit around the tunnel 24. The ring parts (ends thereof) could attach to each other, for example, or snap fit around the tunnel. The center ring 21 may be made of any number of suitable materials, such as thermoplastic elastomers, other plastics, silicone, and the like, and tabs 22 are preferably constructed of like material as desired. Each tab 22 is provided at its distal end with an adhesive portion 25. Once the breastshield 20 is positioned on the breast, the release paper 26 is removed from each tab 22, and the tabs 22 are adhered to the skin, in a three-point mounting arrangement.

Figure 3A:
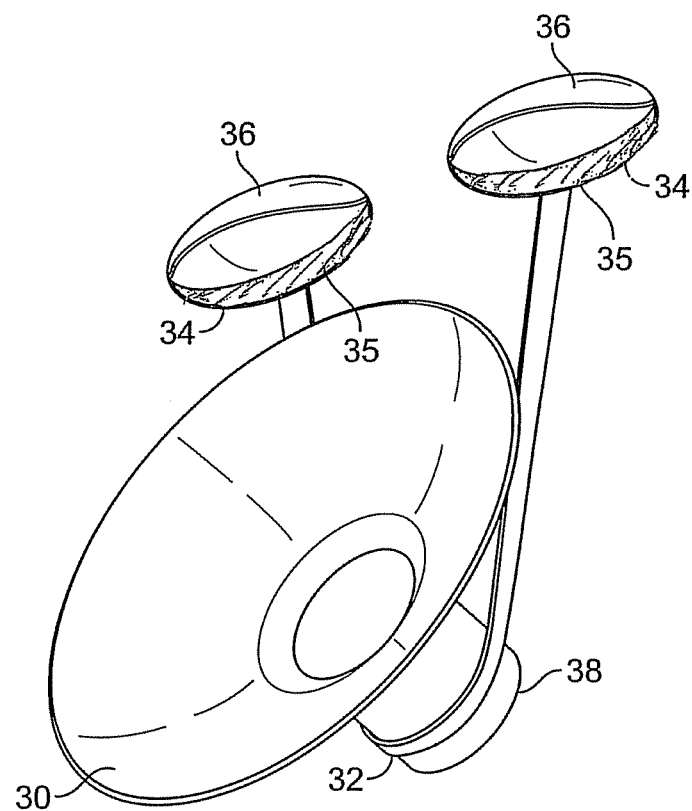
FIG. 3(a) is a perspective view of a third embodiment made in accordance with the present invention.

FIGS. 3(a) and (b) depict yet another embodiment of the present invention. To secure the breastshield 30 to a mother's breast, a support strap 32 is provided with pads 34 at each end. The support strap and pad are preferably constructed of fabric, plastic or any number of other materials ordinarily used to make lightweight straps. Each pad 34 is provided with a layer of adhesive 35 on one side and a release paper 36. Once the breastshield 30 placed on the breast, the release paper 36 from one of the adhesive pads 34 is removed and that pad is affixed to the breast. The support strap 32 then is directed in a downwardly direction, passed under the nipple tunnel 38, and then directed in an upwardly direction. The release paper 36 from the remaining pad 34 is then removed, and the remaining pad 34 is affixed to the breast. The pads need not be positioned in any specific location on the breast or upper torso, other than being located generally above the nipple tunnel of the breastshield so as to form a sling-like support. Note that a cross-over arrangement of the strap ends may be advantageous.

Figure 4:
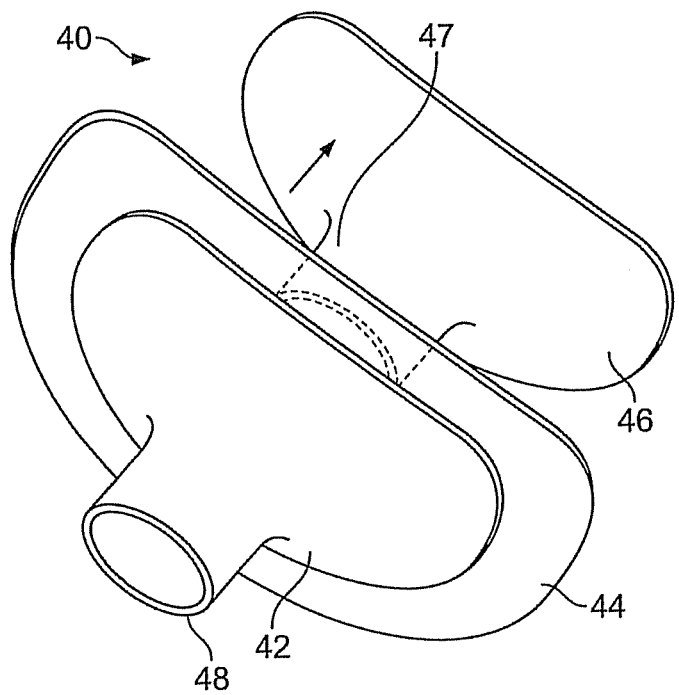
FIG. 4 is a perspective, partially exploded view of a fourth embodiment made in accordance with the present invention.

The embodiment of FIG. 4 depicts a two-part breastshield assembly 40 including a plastic molded sleeve 42 having a ring of adhesive 44 about its circumference that is to be placed over a breastshield 46. While it is described as molded, it could be made otherwise (for instance, formed paper or the like, for a disposable sleeve). In use, the sleeve 42 fits over the breastshield 46, and is pressed against the breast for the adhesive 44 to adhere the assembly to the breast. After the pumping session is completed, the sleeve 42 is removed from the breast, and disposed of (if made disposable) while the breastshield insert is retained for the next pumping session.

This FIG. 4 version is shown adapted for a breast shield that is reversibly attached to a base portion of the breastpump assembly (e.g., a collar within which or over which the nipple tunnel is received). Alternatively, the sleeve could be made with a longitudinal slit or the like, so as to wrap around a shield made integral (non-removable) with the rest of the breastpump assembly.

It will further be noted that when this and various other embodiments are referred to as being attached to the breast with the adhesive, that attachment may often extend beyond the breast to the adjacent chest region (indeed there may be no adhesive fixation directly to the breast at all in some instances).

Figure 5A:
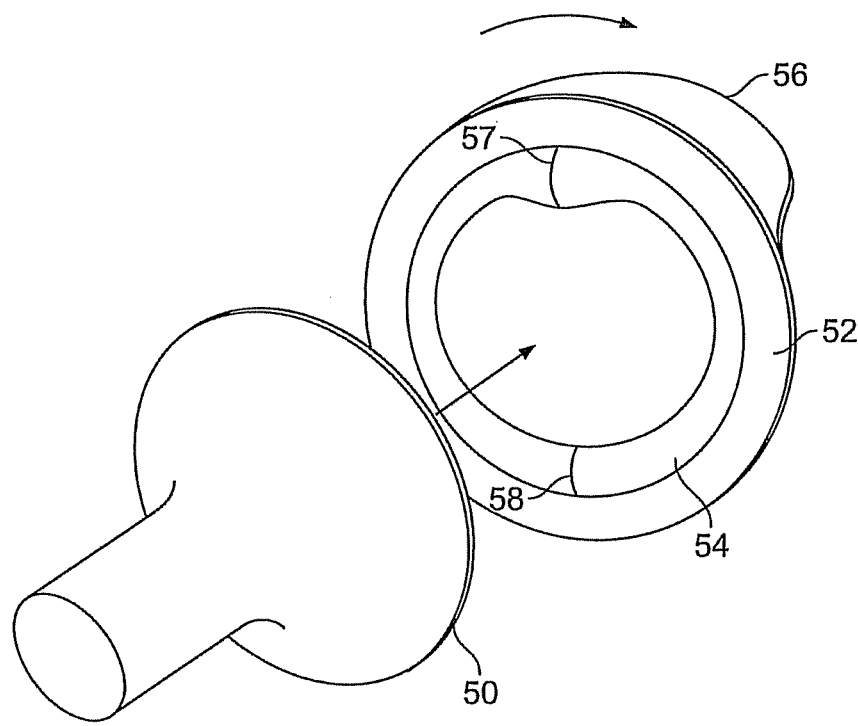
FIG. 5(a) is a perspective, partially exploded view of a fifth embodiment made in accordance with the present invention.

In the embodiment of FIGS. 5(a) and (b), a breastshield 50 is used with a mounting ring 52 having a flange 54 positioned along some (or all) of the ring's inner circumference. The ring 52 preferably takes the form of a thin piece of hard plastic, and the flange 54 is preferably constructed of a soft or more pliable material such as a thermoplastic elastomer (TPE). Adhesive (not shown) is provided along one side of the ring 52 and is covered with release paper 56.

Figure 5B:
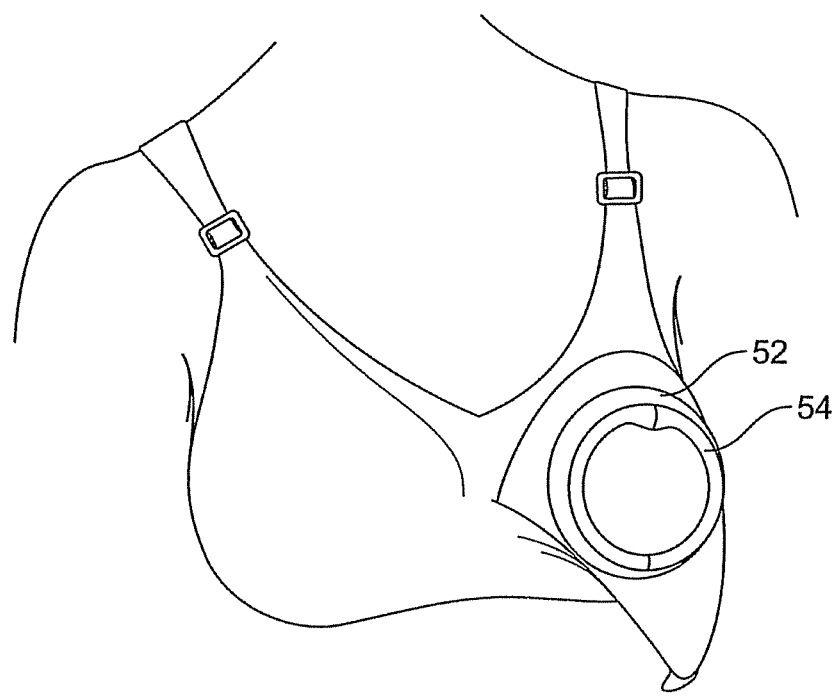
FIG. 5(b) is a perspective view of the ring of the fifth embodiment adhered to a mother's breast.

In use, the release paper 56 is removed from the ring 52, and the ring 52 is positioned around the mother's breast and secured thereto with the adhesive, as shown in FIG. 5(b). The outer perimeter of the breastshield 50 is then fit or wedged behind the flange 54. The flange 54 may be provided with a lip 57 to help retain the breastshield in place. The lip may be of a more rigid material. Further, the flange 54 may be provided with a slit 58 to facilitate the insertion of the perimeter of the breastshield behind the flange 54. The breastshield is tipped under the lip 57, and then manipulated behind the flange 54.

Figure 5C:
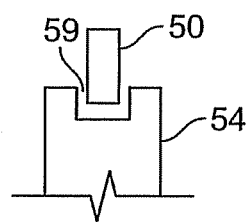
FIG. 5(c) is a cross-sectional view of an annular lip of the fifth embodiment of the present invention taken along line 5-5 of FIG. 5(a)

Alternately, the flange 54 may be provided with an annular lip 59 into which the perimeter of the breastshield 50 fits, as shown in FIG. 5(c). After the pumping session is completed, the breastshield is removed and the adhesive ring 52 may remain on the mother's breast all day. The ring is constructed of such a material as to be comfortable to wear all day and can have a low profile that allows the ring to be less apparent under clothing.

As still another variation on the foregoing, the adhesive ring 52 could be placed (in whole or in part) not on a mounting ring but directly on/around the breast. For example, a ring (or partial ring) of double-sticky tape or the like could be provided. This tape ring is then put in place on the breast/torso, and the release paper on the now-outboard side removed to attach the breastshield. The tape ring could conceivably be left in place, with the release paper re-covering the tape ring between uses.

Figure 6A:
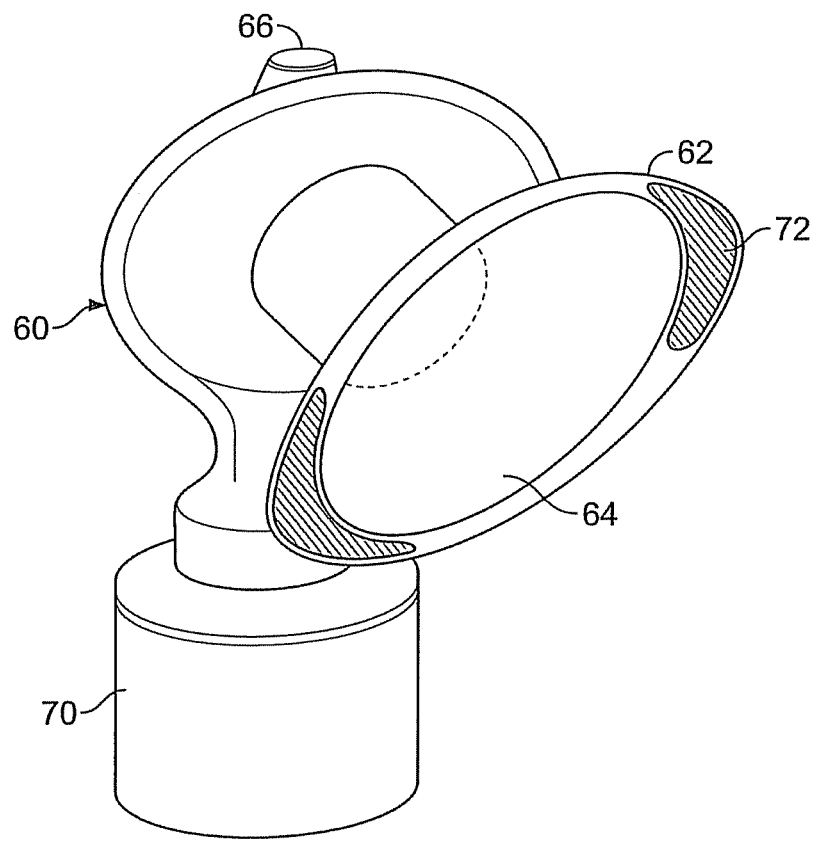
FIG. 6(a) is a perspective view of a sixth embodiment made in accordance with the present invention.
Figure 6B:
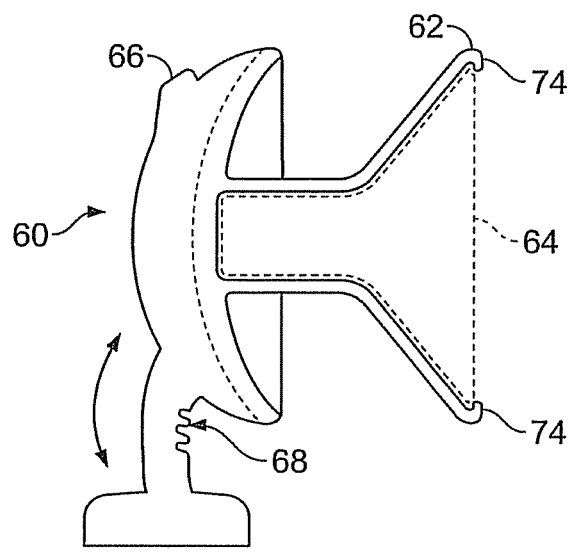
FIG. 6(b) is a cross-sectional view of the sixth embodiment of the present invention.
Figure 6C:
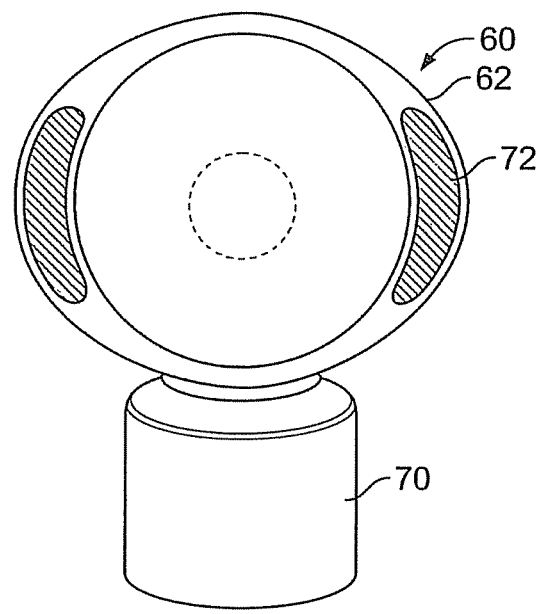
FIG. 6(c) is a front view of the sixth embodiment of the present invention (as viewed in use)

The embodiment of FIGS. 6(a)-(c) is directed to a breastpump assembly 60 having a shield part 62 preferably made of silicone and an inner shield part 64 made of a hard plastic such as polypropylene. The assembly 60 includes a vacuum connection port 66 (for tubing) and a flexible conduit structure and collar 68 for attachment to a collection bottle 70. While the details of the breastpump assembly are not significant, beyond the interaction with the various support means described herein, one can refer to pending U.S. patent application Ser. No. 11/591,276 for this embodiment. As seen in FIG. 6(a), the shield part 62 is provided with areas 72 for adhesive. The adhesive may be applied using glue supplied separately for this purpose. The adhesive may be provided on areas 72 and moisture activated, for another instance. Such moisture activated adhesives are known, and many can be reactivated numerous times. The breastpump assembly 60 is then placed over the mother's breast and held in place by the adhesive.

Figure 7A:
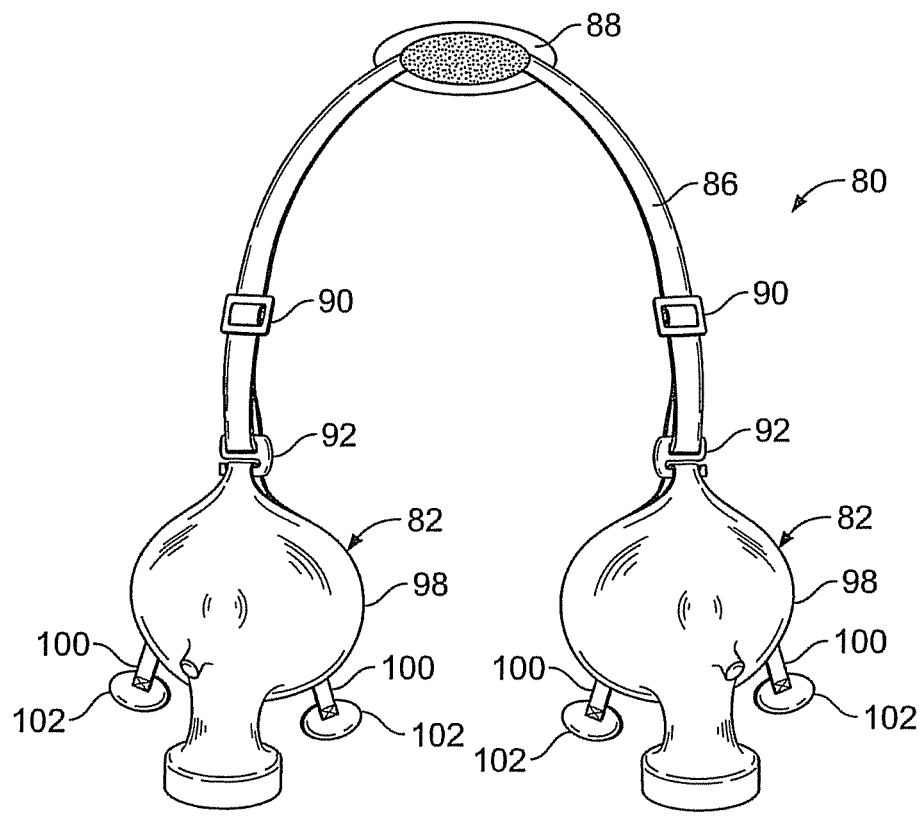
FIG. 7(a) is a rear (back) view of the seventh embodiment made in accordance with the present invention (as viewed in use)

FIG. 7(a) represents a further embodiment of the present invention that provides a system 80 for hands free simultaneous expression of milk from both breasts. Two breastpump assemblies 82 (similar to that of FIGS. 6(a)-6(c)) are connected via a neck strap 86 that is intended to be worn around a mother's neck. For the mother's comfort, the neck strap 86 is provided with a pliable pad 88, preferably made of silicone, and strap retainers 90 for adjusting the height of the strap to accommodate the specific physiology of a particular mother. Each end of the neck strap 86 is provided with a clip 92 with a portion fitting into a loop or slot in the breastshield (or its base), that allows the respective breastshield to be removed from the strap 86.

Figure 3B:
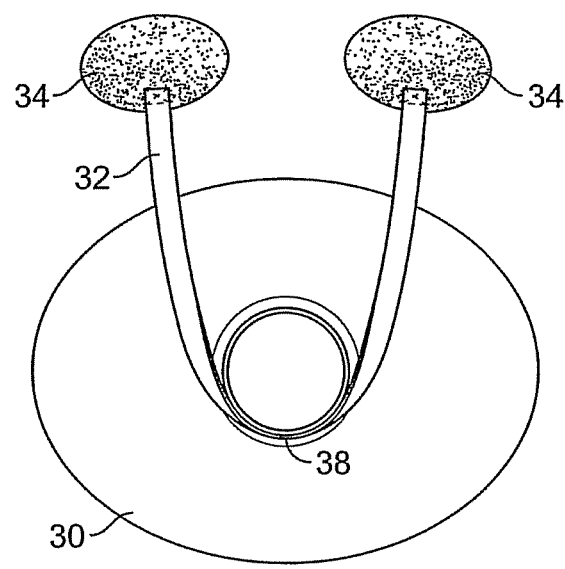
FIG. 3(b) is a rear (back) view of the third embodiment of the present invention (as viewed in use)
Figure 7B:
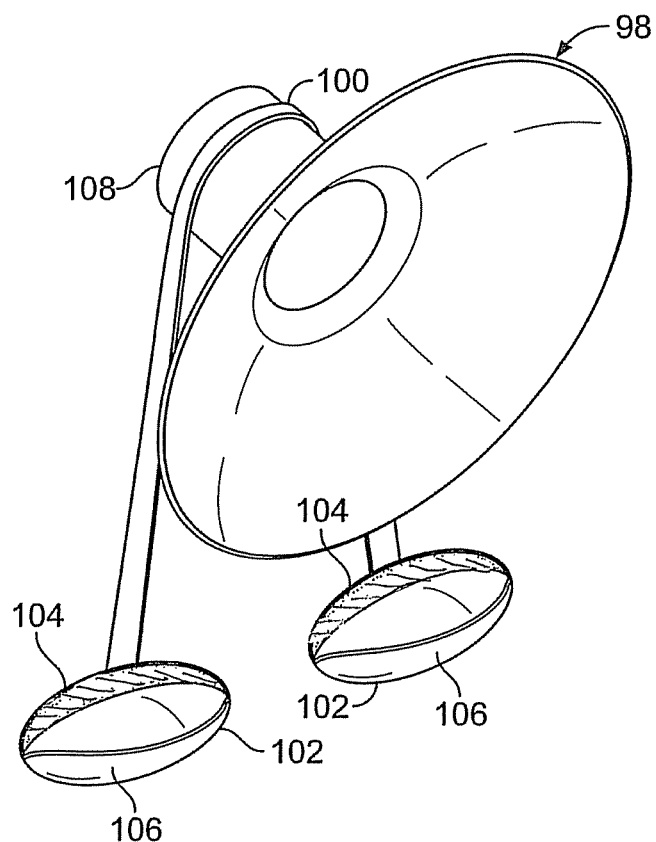
FIG. 7(b) is a perspective view of the insert used with the seventh embodiment of the present invention.

Each breastpump assembly 82 has a shield 98, shown best in FIGS. 7(b) and (c), made of a hard plastic such as polypropylene. Each shield 98 is provided with a support strap 100 having pads 102 at each end. The support strap 100 and the pads 102 may be constructed of fabric, plastic or any number of other materials ordinarily used to make lightweight straps. Each pad 102 is provided with a layer of adhesive 104 on one side and a release paper 106 covering the adhesive. These straps-with-pads are virtually the same as described with respect to FIGS. 3(a)-3(b).

In use, the shields 98 are placed on the breast. The neck strap 86 is placed about a mother's neck. The support strap 100 is, in this embodiment, draped over the nipple tunnel 108 of the shield insert 98, and the pads 102 affixed to the breast below the level of the nipple tunnel upon removal of the release paper 106. The pads need not be positioned in any specific location on the breast other than generally being located below the nipple tunnel of the breastshield so as to provide this three-point fixation. The support strap 100 and the adhesive pads 102 keep each shield 98 in the desired place.

Figure 8:
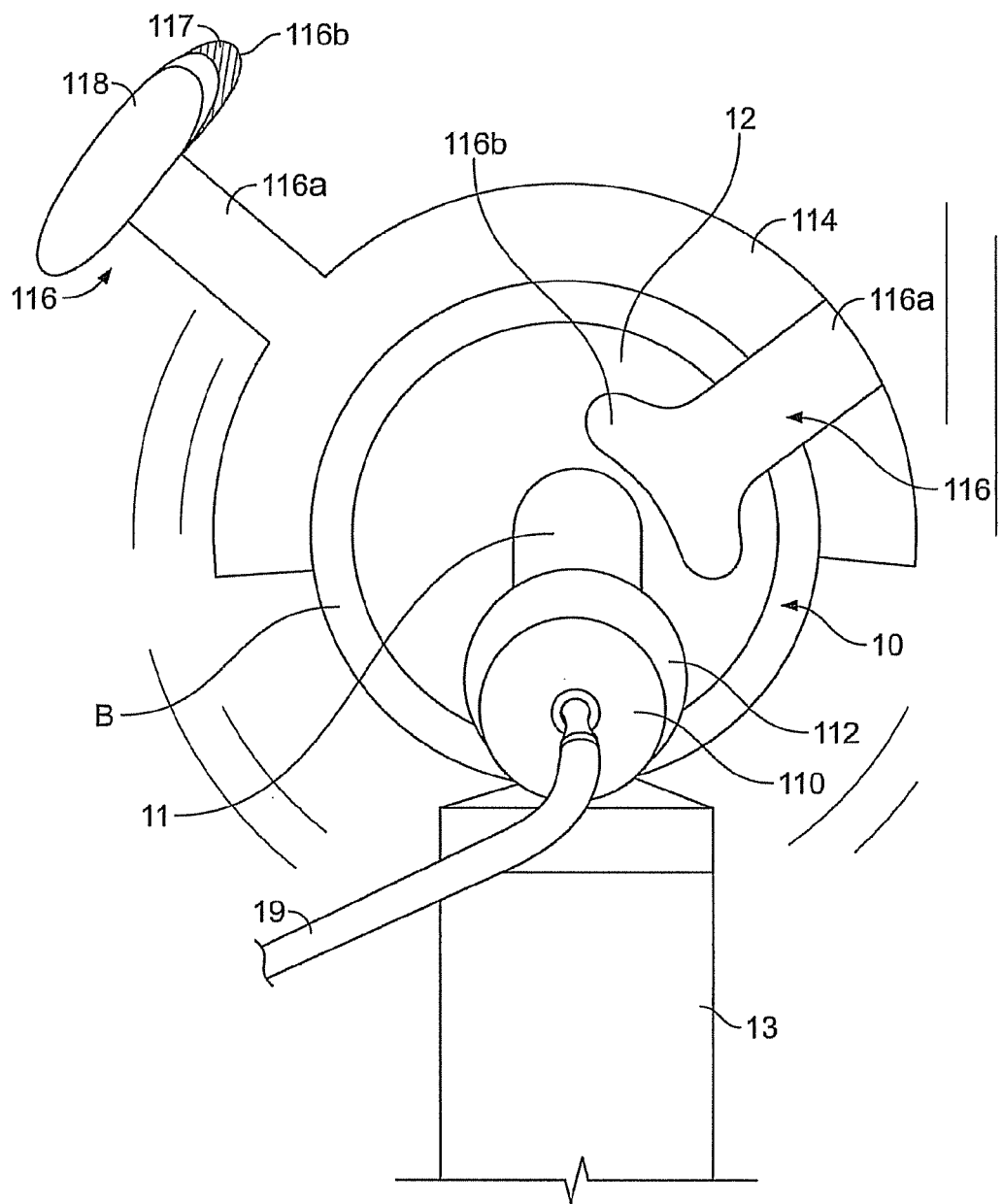
FIG. 8 is a front view of yet another embodiment of the present invention (as viewed in use).

FIG. 8 shows yet another embodiment using a tape-type adhesive attachment device. Depicted is a breastpump assembly much like that of FIG. 1, although this one uses a standard adapter 110 that screws into the collar 112 of the breastpump (converting it from a manual piston pump to a motor-driven application). This breastshield 10 is held in place using a partial ring member (base) 114 which has wings 116 extending therefrom. The base 114 has an adhesive backing covered by a release element (for example, like that used with an adhesive wound-type dressing). The base is shown here in FIG. 8 after the release element has been removed, and the base adhered to the torso about the breast B. Wings 116 have elongate extensions 116a terminating in adhesive pads 116b. Pads 116b have an adhesive layer 117 with a release element covering 118, again much like that used for the foregoing wound dressing. In use, the release element 118 is removed, and the extension folded at the joint with the base 114 for attachment to the outboard side of the breastshield central portion 12.

Figure 7C:
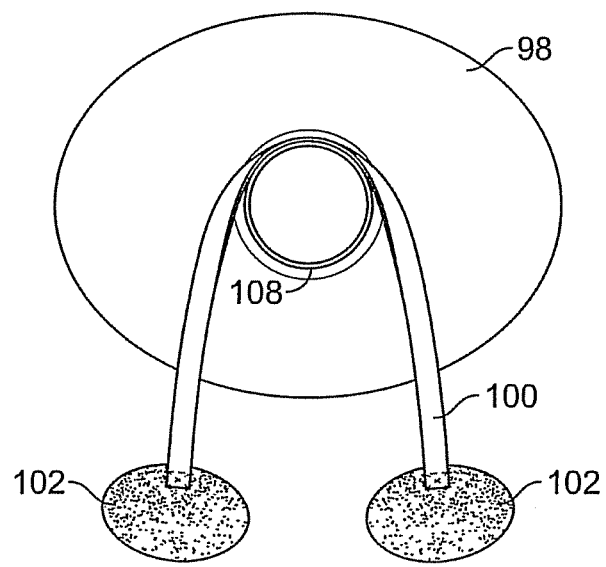
FIG. 7(c) is a rear (back) view of the insert used with the seventh embodiment of the present invention (as viewed in use)

The present invention does not require the use of a specific type of adhesive to be used. Rather, the adhesive must be strong enough to support the weight of the breastshield, a collection bottle, and 5 ounces of milk in those versions not using some other component for support (such as in FIGS. 7(a)-7(c)). It is also desirable for the adhesive to be reusable in certain embodiments, and to adhere to skin that is slightly moist. It is further advantageous for the adhesive to be of a type that is readily removed from the breast with the breastshield, and most preferably without leaving any significant residue. The adhesive may take the form of a thin pad, as shown in FIG. 1(a), double-sided sticky member, moisture activated glue, a gel that may be applied to the surface of the skin or the interior surface of a breastshield, or a flowable liquid that may be rolled onto the skin or the interior surface of a breastshield, just to name a few examples, all well-known in the art.

Adhesives considered suitable, but without being limited thereto, would be of the type used for attachable breast forms, such as on the Trulife Harmony "Connect" product, and the adhesive used on the NuBra "Aphrodite" bra product. Wonderful Breast, Inc. provides a roll-on adhesive product called "It Stays," and double-sided tapes for garment securement. Avery Dennison Medical's MED 5717P product has a non-sensitizing acrylic pressure-sensitive adhesive including Kraft-paper release liner that may be used. 3M provides a foam tape using an acrylate adhesive, such as Foamtape 9973 and 9772L. Coloplast uses a double-layered adhesive for its ostomy products that should be adaptable to use with the present invention. Chen U.S. Pat. No. 6,780,081 can be looked to for pressure-sensitive adhesive materials in the environment of the invention.

While certain features and embodiments of the present application have been described in detail herein, it is to be understood that the application encompasses all modifications and enhancements within the scope and spirit of the following claims.

What is claimed is:

1. A method of supporting a breastshield on a breast for breastmilk pumping wherein the method comprises providing a breastshield, said breastshield having a generally concave-shaped part within which a woman's breast is received, and a milk conduit for conveying milk to a milk container; and adhesively securing the breastshield to the mother's torso using an adhesive applied to said concave-shaped part, which is compatible with application on human skin, the adhesive securement is sufficiently strong to independently support the breastshield and the related milk container in place without any other means of support throughout a breast pumping session.

2. The method of claim 1 wherein said breastshield has an inboard surface contacting the woman's breast, and said adhesive securement is provided by an adhesive portion on said inboard surface of said breastshield.

3. The method of claim 2 wherein said adhesive portion is a moisture activated glue.

4. The method of claim 2 wherein said adhesive portion is covered by a release element prior to use.

5. The method of claim 1 wherein said adhesive securement is a double-sided sticky member that is provided separate from the breastshield before use, the method further comprising the step of applying the double-sided sticky member to the breastshield prior to the adhesively securing step.

6. The method of claim 1 wherein said adhesive securement is a flowable contact adhesive that is applicable to the breast, the breastshield, or both, the method further comprising the step of applying the flowable contact adhesive to the breast, the breastshield, or both, prior to the adhesively securing step.

7. A support member for use with a breastpump for supporting a breastshield of the breastpump in place on a woman's breast wherein said support member has a part to which an adhesive is applied, said support member is adhesively secured to the woman's torso, provides the sole means of support for said breastshield, and is positioned annularly about the breastshield.

8. The support member of claim 7 comprising an outer sleeve that fits over an exterior of said breastshield, said outer sleeve being provided with an adhesive portion for supporting said breastshield in place.

9. The support member of claim 8 wherein the outer sleeve is disposable.

10. The support member of claim 7 comprising a double-sided sticky member that is provided separate from the breastshield before use.

11. The support member of claim 7 comprising a pad that is placed over a portion of the breastshield, the pad being provided with an adhesive for supporting said breastshield in place.

12. The support member of claim 11 wherein the pad extends beyond at least part of a perimeter of said breastshield.

13. A support member for use with a breastpump for supporting a breastshield of the breastpump in place on a woman's breast wherein said support member is adhesively secured to the woman's torso using an adhesive which is compatible with application to human skin, and provides the sole means of support for said breastshield, the support member comprising an annular ring fitting about said breastshield, said annular ring having tabs extending outwardly therefrom, an adhesive portion being provided on each of said tabs.

14. A support member for use with a breastpump for supporting a breastshield of the breastpump in place on a woman's breast wherein said support member is adhesively secured to the woman's torso using an adhesive which is compatible with application to human skin, and provides the sole means of support for said breastshield, the support member comprising a ring fitting about said breastshield, said ring having tabs extending outwardly therefrom, an adhesive portion being provided on each of said tabs, wherein said ring is split for positioning about said breastshield.

15. A support member for use with a breastpump for supporting a breastshield of the breastpump in place on a woman's breast wherein said support member has a part to which an adhesive is applied, said support member is adhesively secured to the woman's torso, provides the sole means of support for said breastshield, and is positioned about the breastshield, the support member comprising a strap having an adhesive portion on each end of said strap, said strap passing under a nipple tunnel of said breastshield, and said ends being adhesively secured to the mother's torso to support said breastshield in place.

16. The support member of claim 15 wherein said strap ends are positionable at a location on the breast that is above said nipple tunnel of the breastshield.

17. A support member for use with a breastpump for supporting a breastshield of the breastpump in place on a woman's breast wherein said support member is adhesively secured to the woman's torso using an adhesive which is compatible with application to human skin, and provides the sole means of support for said breastshield, the support member comprising a mounting ring for placement on the breast, an adhesive portion being provided on said ring, said breastshield having a perimeter part that is received and held within said ring in use.

18. The support member of claim 17 wherein said ring further comprises a flange about an inner circumference, said flange supporting said breastshield in place.

19. The support member of claim 18 wherein said flange further comprises a lip under which said breastshield is received for supporting said breastshield in place.

20. The support member of claim 17 wherein said ring has an annular channel formed interiorly thereto, within which said perimeter part is received.

* * * * *